US012406231B2

(12) United States Patent
Grishina et al.

(10) Patent No.: US 12,406,231 B2
(45) Date of Patent: Sep. 2, 2025

(54) SYSTEM AND METHOD FOR IMPROVED SPARE PART SEARCH FOR MAINTENANCE SERVICES USING TOPIC MODELLING

(71) Applicant: KONINKLIJKE PHILIPS N.V., Eindhoven (NL)

(72) Inventors: Anastasiia Grishina, Eindhoven (NL); Milosh Stolikj, Eindhoven (NL); Qi Gao, Eindhoven (NL); Milan Petkovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 321 days.

(21) Appl. No.: 18/017,098

(22) PCT Filed: Jul. 21, 2021

(86) PCT No.: PCT/EP2021/070309
§ 371 (c)(1),
(2) Date: Jan. 20, 2023

(87) PCT Pub. No.: WO2022/018104
PCT Pub. Date: Jan. 27, 2022

(65) Prior Publication Data
US 2023/0298086 A1    Sep. 21, 2023

Related U.S. Application Data

(60) Provisional application No. 63/055,528, filed on Jul. 23, 2020.

(51) Int. Cl.
G06Q 30/00    (2023.01)
G06N 5/04     (2023.01)
(Continued)

(52) U.S. Cl.
CPC ............... *G06Q 10/20* (2013.01); *G06N 5/04* (2013.01); *G06Q 10/0875* (2013.01); *G06Q 30/0631* (2013.01); *G16H 40/40* (2018.01)

(58) Field of Classification Search
None
See application file for complete search history.

(56) References Cited

U.S. PATENT DOCUMENTS

2004/0019534 A1*  1/2004  Callahan ............ G06Q 30/0643
                                                        705/26.8
2007/0250229 A1* 10/2007  Wu ........................ G06Q 10/06
                                                         701/31.4
(Continued)

FOREIGN PATENT DOCUMENTS

WO    2019/169147 A1    9/2019
WO    2019/243291 A1   12/2019
WO    2020/260121 A1   12/2020

OTHER PUBLICATIONS

Improving spare part search for maintenance services using topic modelling, Author: Grishina, Anastasiia1, et al., Publication info: CEUR Workshop Proceedings 2699CEUR-WS. (2020). (Year: 2020).*

(Continued)

*Primary Examiner* — Matthew T Sittner (57) ABSTRACT

A recommendation method (200) includes: querying a knowledge base (130) of maintenance cases using the text query to retrieve a ranked list (138) of maintenance cases relating to a text query; performing topic modeling (140) on the maintenance cases of the ranked list of maintenance cases to group the maintenance cases into N topics; for each topic, ranking the replaced part identifiers associated to the maintenance cases grouped into that topic to generate a ranked replaced part identifiers list (142) for that topic; displaying summarization (144) of the N topics on the display of the user interface and receiving a selection of a (Continued)

selected topic of the N topics via the user interface device; and displaying a list (150) of recommended parts for replacement comprising at least a top portion of the ranked replaced part identifiers list for the selected topic on the display of the user interface device.

6 Claims, 5 Drawing Sheets

(51) Int. Cl.
    *G06Q 10/0875*     (2023.01)
    *G06Q 10/20*     (2023.01)
    *G06Q 30/0601*     (2023.01)
    *G16H 40/40*     (2018.01)

(56) References Cited

U.S. PATENT DOCUMENTS

| | | | | |
|---|---|---|---|---|
| 2009/0204232 A1* | 8/2009 | Guru | ............ | G06Q 10/08 700/12 |
| 2013/0218400 A1* | 8/2013 | Knoop | ............ | G07C 5/006 701/31.4 |
| 2018/0111278 A1* | 4/2018 | Godlieb | ............ | B26B 19/388 |
| 2020/0042930 A1 | 2/2020 | Cappitelli | | |
| 2021/0357766 A1* | 11/2021 | Paul | ............ | G06N 5/02 |

OTHER PUBLICATIONS

A flexible control system for flexible manufacturing systems, Author: Scott, Wesley Dane. Publication info: Texas A&M University. ProQuest Dissertations & Theses, 2004. (Year: 2004).*

International Search Report and Written Opinion Dated Nov. 4, 2021 for International Application No. PCT/EP2021/070309 Filed Jul. 21, 2021.

Grishina, et al: "Improving Spare Part Search for Maintenance Services using Topic Modelling", Proceedings of the CIKM 2020 Workshops, Oct. 19-20.

Moharana, et al: "Determination of optimal kit for spare parts using association rule mining", International Journal of System Assurance Engineering and Management, vol. 6, No. 3, Jun. 17, 2014.

Manning, et al: "Introduction to Information Retrieval", Cambridge University Press, Cambridge, 2008 https://doi.org/10.1017/CBO9780511809071.

Robertson, et al: "Okapi at TREC-3", Proceedings of the Third Text Retrieval Conference (1994).

Blei, et al: "Latent Dirichlet Allocation", Journal of Machine Learning Research 3 (2003), 993-1022).

* cited by examiner

| Metric@K | K=5 | | K=10 | | Best possible values |
|---|---|---|---|---|---|
| | Baseline | LDA | Baseline | LDA | |
| completeness | 0.538 | 0.566 ± 0.0037 | 0.564 | 0.584 ± 0.0017 | 0.601 |
| recall | 0.559 | 0.595 ± 0.0047 | 0.592 | 0.617 ± 0.0027 | 0.641 |
| success | 0.590 | 0.633 ± 0.0064 | 0.627 | 0.657 ± 0.0025 | 0.685 |
| min_top_k | 1.347 | 1.250 ± 0.0267 | 1.649 | 1.471 ± 0.0462 | n/a |
| Metric improved in % of test queries | | | | | |
| completeness | n/a | 2.86 ± 0.39 | n/a | 2.06 ± 0.20 | n/a |
| recall | n/a | 5.45 ± 0.55 | n/a | 3.84 ± 0.60 | n/a |
| success | n/a | 4.48 ± 0.50 | n/a | 3.03 ± 0.48 | n/a |
| min_top_k | n/a | 10.50 ± 0.57 | n/a | 11.85 ± 0.98 | n/a |

SYSTEM AND METHOD FOR IMPROVED SPARE PART SEARCH FOR MAINTENANCE SERVICES USING TOPIC MODELLING

CROSS REFERENCE TO RELATED APPLICATIONS

This application is the U.S. National Phase application under 35 U.S.C. § 371 of International Application No. PCT/EP2021/070309 filed Jul. 21, 2021, which claims the benefit of U.S. Provisional Patent Application No. 63/055,528 filed Jul. 23, 2020. These applications are hereby incorporated by reference herein.

FIELD

The following relates generally to the servicing and maintenance arts, especially as directed to medical imaging device servicing or the servicing of other complex systems, maintenance history analysis arts, and related arts.

BACKGROUND

The maintenance of medical imaging systems (e.g., magnetic resonance (MR), positron emission tomography (PET), computed tomography (CT), interventional—X ray, etc.) or other complex machinery or systems such as commercial aircraft, railroad engines, industrial machines, or the like, can be complex. In particular, the ordering of correct replacement or updated parts can be complex.

To support decision-making process in various industrial applications, many companies use knowledge management and Information Retrieval (IR). In an industrial setting, such as for medical device maintenance, knowledge is extracted from data that is often stored in a semi-structured or unstructured format. As a result, Natural Language Processing (NLP) methods have been applied to a number of IR tasks.

Currently, replacement part maintenance for medical devices can be performed in a variety of ways, one of which is the replacement of one or more malfunctioning parts. However, remedying the underlying problem of the medical device may need the replacement of multiple parts, which may not be obvious to a service engineer performing the device maintenance.

The following discloses certain improvements to overcome these problems and others.

SUMMARY

In one aspect, a parts ordering system operative in conjunction with a knowledge base of maintenance cases for devices under maintenance wherein the maintenance cases have associated replaced part identifiers includes: a user interface device including a display and at least one user input device. An electronic processor is programmed to perform a recommendation method for recommending parts for replacement during maintenance of a device currently under maintenance. The recommendation method includes: receiving a text query relating to the maintenance of the device currently under maintenance via the user interface device; querying the knowledge base of maintenance cases using the text query to retrieve a ranked list of maintenance cases relating to the text query; performing topic modeling on the maintenance cases of the ranked list of maintenance cases to group the maintenance cases into N topics, where N is an integer greater than or equal to two; for each topic, ranking the replaced part identifiers associated to the maintenance cases grouped into that topic to generate a ranked replaced part identifiers list for that topic; displaying summarizations of the N topics on the display of the user interface and receiving a selection of a selected topic of the N topics via the user interface device; and displaying a list of recommended parts for replacement comprising at least a top portion of the ranked replaced part identifiers list for the selected topic on the display of the user interface device.

In another aspect, a non-transitory computer readable medium stores instructions executable by at least one electronic processor to perform a recommendation method for recommending parts for replacement during maintenance of a device currently under maintenance. The recommendation method includes: receiving a text query relating to the maintenance of the device currently under maintenance via a user interface device; querying a knowledge base of maintenance cases for devices under maintenance wherein the maintenance cases have associated replaced part identifiers using the text query to retrieve a ranked list of maintenance cases relating to the text query; performing topic modeling on the maintenance cases of the ranked list of maintenance cases to group the maintenance cases into N topics, where N is an integer greater than or equal to two; for each topic, ranking the replaced part identifiers associated to the maintenance cases grouped into that topic to generate a ranked replaced part identifiers list for that topic; displaying summarizations of the N topics on the display of the user interface and receiving a selection of a selected topic of the N topics via the user interface device; and displaying a list of recommended parts for replacement comprising at least a top portion of the ranked replaced part identifiers list for the selected topic on a display of the user interface device.

In another aspect, a method for recommending parts for replacement during maintenance of a device currently under maintenance includes: receiving a text query relating to the maintenance of the device currently under maintenance via a user interface device; querying a knowledge base of maintenance cases for devices under maintenance wherein the maintenance cases have associated replaced part identifiers using the text query to retrieve a ranked list of maintenance cases relating to the text query; performing topic modeling on the maintenance cases of the ranked list of maintenance cases to group the maintenance cases into N topics, where N is an integer greater than or equal to two; for each topic, ranking the replaced part identifiers associated to the maintenance cases grouped into that topic to generate a ranked replaced part identifiers list for that topic; displaying summarizations of the N topics on the display of the user interface and receiving a selection of a selected topic of the N topics via the user interface device; and displaying a list of recommended parts for replacement comprising at least a top portion of the ranked replaced part identifiers list for the selected topic on a display of the user interface device. The displaying of the list of recommended parts for replacement is included in a parts ordering user interface presented on the user interface device, and the method further includes: receive a selection of one or more part identifiers via the parts ordering user interface and to connect via an electronic network with a parts ordering system to order one or more parts corresponding to the selected one or more part identifiers.

One advantage resides in providing enhanced performance of an industrial entity retrieval system by learning semantic correspondences between short historical descriptions of events associated with the entities.

Another advantage resides in providing a spare parts retrieval mechanism in remote system diagnostics and maintenance of industrial equipment using topic modelling to group extracted historical cases and parts under topics that should represent failure root causes.

Another advantage resides in providing a spare parts retrieval mechanism using customized information retrieval metrics.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

The following relates to using NLP, and particularly topic modelling, to improve spare part retrieval in the context of medical equipment maintenance. In particular, the following discloses how remote (or, alternatively, on-site) system diagnostics can be used when medical equipment malfunctions, i.e. stops working according to specification.

In some embodiments disclosed herein, an NLP pipeline is implemented that pre-processes short textual descriptions of maintenance activities. Topic modelling is applied to these descriptions to categorize the descriptions of past cases. The relevant maintenance service reports are grouped into topics using topic modeling. Each topic may be expected to group maintenance cases with similarity to one another, for example, having a common root cause. Once categorized into topics, cases and parts can be easier to examine and more relevant to a particular type of failure.

In some evaluations of the disclosed approach for replacement part(s) recommendation, information retrieval metrics are used that are customized to characterize the relevance and completeness of retrieved entities set. These metrics measure how far in the list of search results all the required parts are present, indicate if at least one required entity is retrieved and whether all needed spare parts are present among top K search results.

Figure 1:
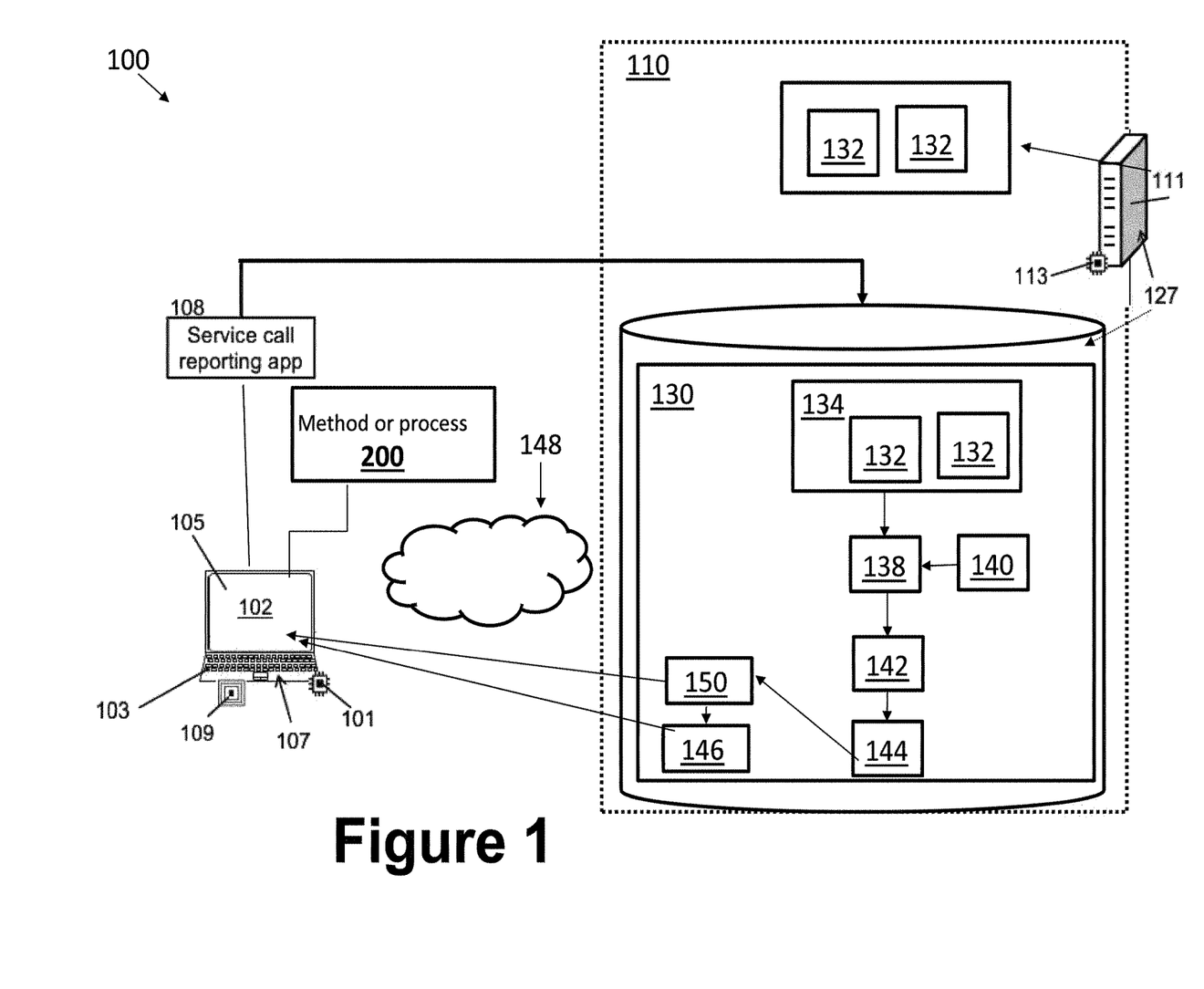
FIG. 1 diagrammatically illustrates an illustrative system for supporting a service engineer in servicing a device in accordance with the present disclosure.

With reference to FIG. 1, an illustrative parts ordering system 100 for supporting a service engineer in servicing a device (e.g., a medical imaging device, not shown—also referred to as a medical device, an imaging device, imaging scanner, and variants thereof) is diagrammatically shown. By way of some non-limiting illustrative examples, the medical imaging device under service may be a magnetic resonance imaging (MRI) scanner, a computed tomography (CT) scanner, a positron emission tomography (PET) scanner, a gamma camera for performing single photon emission computed tomography (SPECT), an interventional radiology (IR) device, or so forth. More generally, the system or device undergoing maintenance may be a medical imaging device, radiation therapy device, or other medical device; or some other complex system such as a commercial aircraft, industrial machine, or the like. As shown in FIG. 1, the servicing support system 100 includes, or is accessible by, a user interface device or a service device 102 carried or accessed by a service engineer (SE). The service device 102 can be a personal device, such as a mobile computer system such as a laptop or smart device. In other embodiments, the service device 102 may be an imaging system controller or computer integral with or operatively connected with the imaging device undergoing service (e.g., at a medical facility). As another example, the service device 102 may be a portable computer (e.g. notebook computer, tablet computer, or so forth) carried by an SE performing diagnosis of a fault with the imaging device and ordering of parts. In another example, the service device 102 may be the controller computer of the imaging device under service, or a computer based at the hospital. In other embodiments, the service device may be a mobile device such as a cellular telephone (cellphone) or tablet computer and the servicing support system 100 may be embodied as an "app" (application program). In another example, the SE may be operating remotely, for example a remote service engineer based at a service center who performs maintenance by advising a customer via telephone as to maintenance operations, and the service device 102 in this case may be a workstation at which the remote service engineer is based. The service device 102 allows the service engineer to interact with the servicing support system via at least one user input device 103 such a mouse, keyboard, or touchscreen. The service device further includes an electronic processer 101 and non-transitory storage medium 107 (internal components which are diagrammatically indicated in FIG. 1). The non-transitory storage medium 107 stores instructions which are readable and executable by the electronic processor 101 to implement the servicing support system 100. The service device 102 may also include a communication interface 109 such that the servicing support system 100 may communicate with a backend server or processing device 111, which may optionally implement some aspects of the servicing support system 100 (e.g., the server 111 may have greater processing power and therefore be preferable for implementing computationally complex aspects of the servicing support system 100). Such communication interfaces 109 include, for example, a wireless Wi-Fi or 4G/5G interface, a wired Ethernet interface, or the like for connection to the Internet and/or an intranet. Some aspects of the servicing support system 100 may also be implemented by cloud processing or other remote processing.

In illustrative FIG. 1, the servicing information collected using a service call reporting app 108 is fed to a database backend 110 (e.g., implemented at a medical facility or other remote center from where the SE is performing the service call, or at the imaging device vendor or other servicing contractor). For example, the database backend 110 stores maintenance cases entered by service engineers to report on servicing performed. The service call reporting app 108 may provide a semi-structured format, for example providing free-text entry fields to be filled in to provide specific information. Some information may be entered using a more structured format, e.g. drop-down boxes, or other user interface dialogs with predefined content. Of note, the maintenance case generated using the service call reporting app 108 includes replaced part identifiers indicating the part or parts replaced in the course of performing the maintenance case. The replaced part identifiers may be entered by the service engineer as part of preparing the maintenance case report, or may in some embodiments be automatically extracted from a parts ordering system, e.g. when a part is ordered it may be automatically associated to the corresponding maintenance case. The reports on the maintenance cases typically include other relevant information such as descriptions of symptoms, description of the conditions under which the problem is observed, description of the diagnostic tests performed, and description of the identified solution or root cause. The backend processing is performed on the backend server 111 equipped with an electronic processor 113 (diagrammatically indicated internal component). The server 111 is equipped with non-transitory storage medium 127 (internal components which are diagrammatically indicated in FIG. 1). While a single server computer is shown, it will be appreciated that the backend 110 may more generally be implemented on a single server computer, or a server cluster, or a cloud computing resource comprising ad hoc-interconnected server computers, or so forth. Furthermore, while FIG. 1 shows a single service device 102, more generally the database backend 110 will receive service call reports from many service devices (e.g., tens, hundreds, or more service devices) carried by different SEs, and each SE will be providing a service call report for each service call that the SE makes (this may total tens or even a few hundred service calls per year by a given SE). Hence, over time the database backend 110 accumulates a large quantity of service call reporting data.

The non-transitory storage medium 127 is configured to store a knowledge base 130 of the maintenance cases for the medical devices generated by the SE's using the service call reporting app 108. As previously noted, the maintenance cases have associated replaced part identifiers 132 corresponding to replacement parts for the medical devices, e.g. as entered by the SE or by auto-populating the replaced part identifiers fields of the maintenance cases from a parts ordering system. In some examples, the knowledge base 130 includes a list 134 of replaced part identifiers 132 associated to each maintenance case. In some examples, the list 134 can be provided manually, e.g., by an SE via the service device 102, by inputting the replaced part identifiers 132 into the service call reporting app 108. In other examples, the list 134 can be mined automatically by comparing a context of an entered maintenance report via the service call reporting app 108 with the replaced part identifiers 132 stored in the knowledge base 130.

The electronic processor 113 of the backend server 111 may optionally be configured to implement a baseline entity retrieval system module 116 programmed to retrieve the replaced part identifiers 132. In this approach, the user (e.g. an SE) inputs a text query relating to the maintenance of the device currently under maintenance via the user interface device 102, and the knowledge base is queried using the text query to retrieve a ranked list of maintenance cases relating to the text query. The replaced part identifiers associated with the retrieved maintenance cases are then presented to the user as a list of recommended parts for replacement, optionally with maintenance case summarization information to provide context. The user can select one or more replacement parts from this list. However, it is recognized herein that this approach has a disadvantage in that the number of retrieved maintenance cases can be large, making it difficult for the user to determine which replacement part(s) are appropriate for the maintenance of the device currently under maintenance.

Accordingly, the electronic processor 113 of the backend server 111 is also preferably configured to implement a topic modelling module 118 programmed to implement a topic modeling process to sort the retrieved maintenance cases into semantic topics. The user can then select the topic most closely related to the maintenance of the device currently under maintenance, and the replaced part identifiers associated only with the retrieved maintenance cases belonging to the user-selected topic are then presented to the user as the list of recommended parts for replacement. The operations of these modules 116, 118 are described in more detail below.

The non-transitory storage medium 127 stores instructions executable by the electronic processor 113 of the backend server 111 to perform a recommendation method or process 200 implemented by the servicing support system 100 for recommending parts for replacement during maintenance of a device currently under maintenance. In some examples, the method 200 may be performed at least in part by cloud processing. The method 200 result in an output of a list 150 of recommended parts for replacement.

Figure 2:
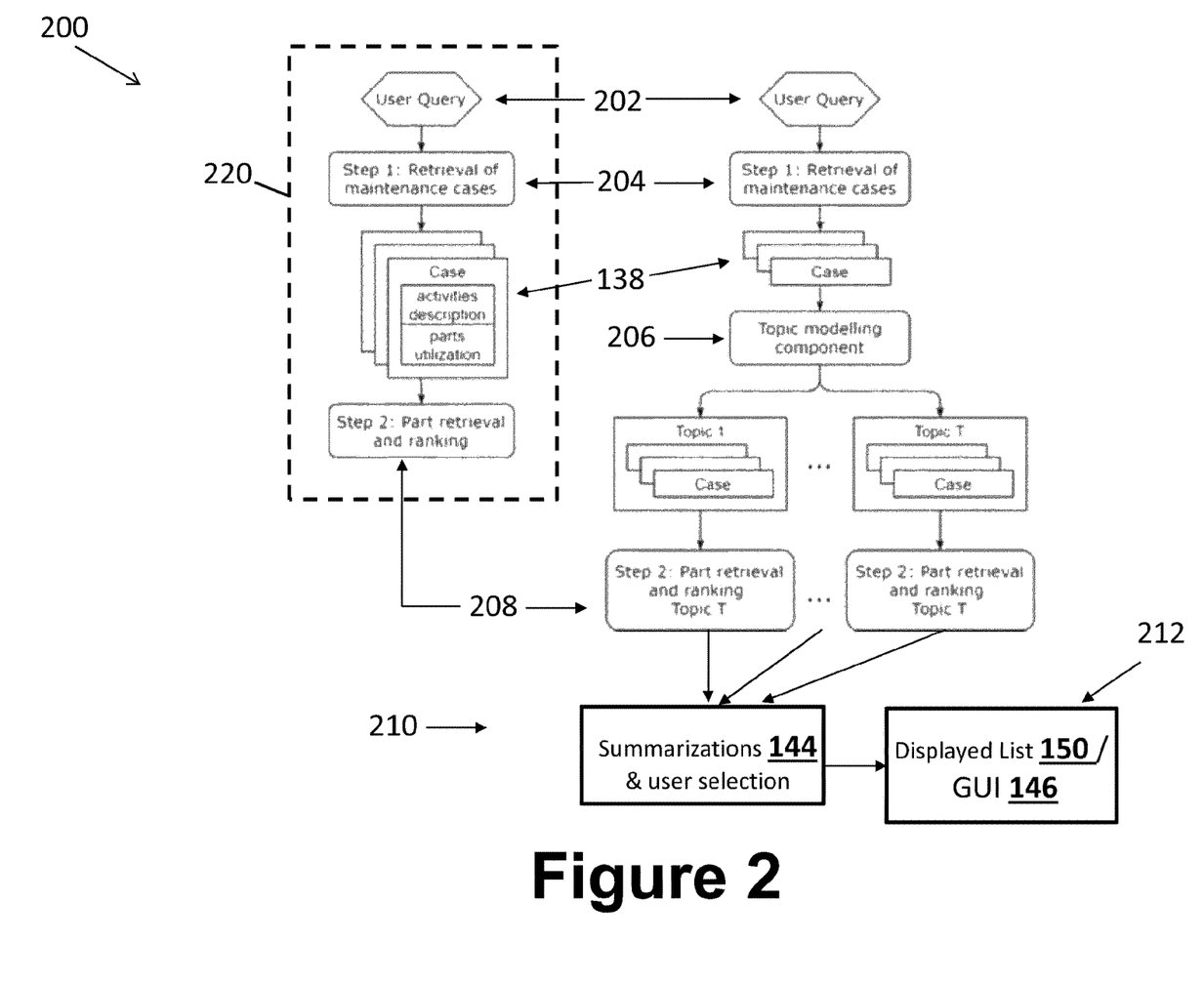
FIG. 2 shows exemplary flow chart operations of the system of FIG. 1.
Figure 3:
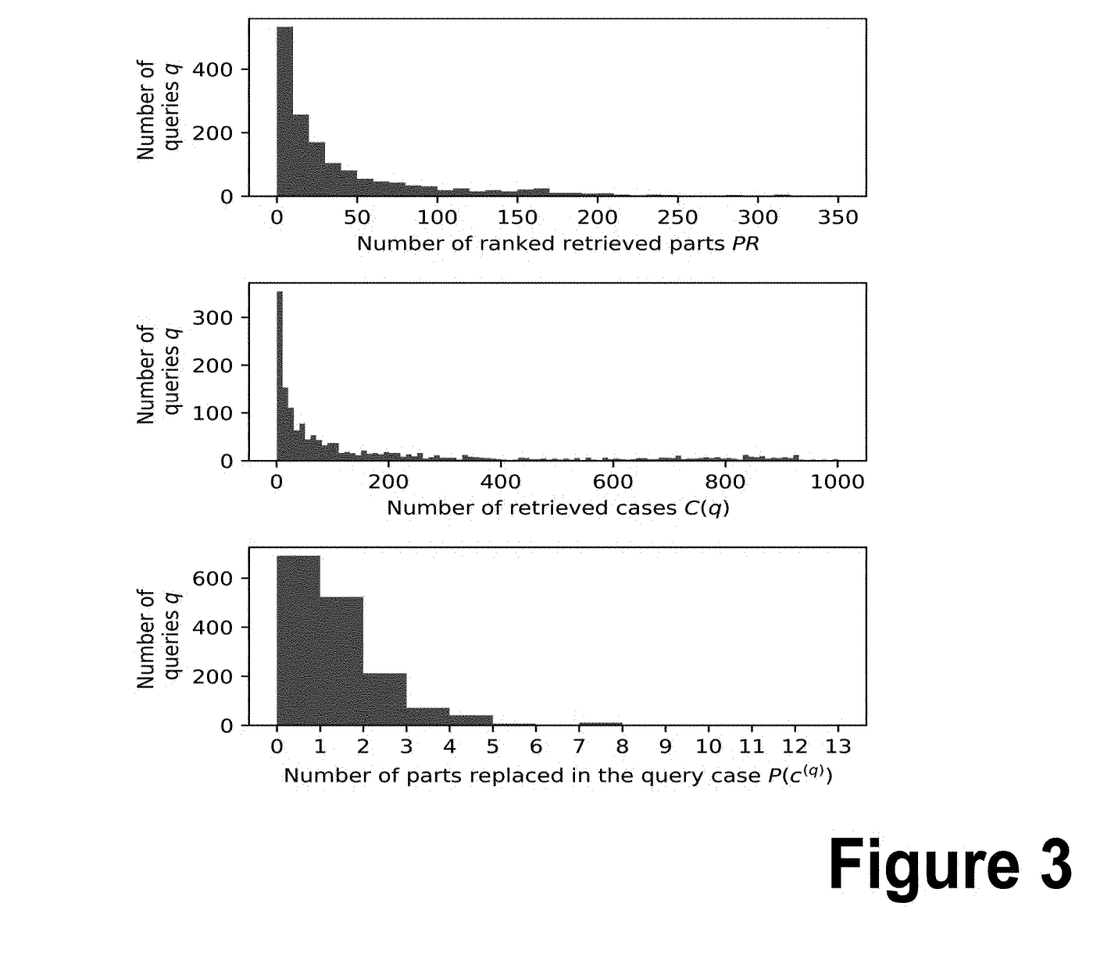
FIGS. 3-5 show statistical representations of data generated by the system of FIG. 1.

With reference to FIG. 2, and with continuing reference to FIG. 1, an illustrative embodiment of an instance of the recommendation method 200 executable by the electronic processor 113 is diagrammatically shown as a flowchart.

At an operation 202, a text query is received by the backend server 111 related to maintenance of the device currently under maintenance via the user interface device 102. This can be performed, for example, by the SE using the user input device 103 to enter and transmit the text query. The text query may include natural language text, numerical text (e.g. model numbers and/or serial numbers of the imaging device and/or parts thereof), At an operation 204, the knowledge base 130 of maintenance cases is queried by the backend sever 111 using the text query to retrieve a ranked list 138 of maintenance cases related to the text query. This operation can be performed by the baseline entity retrieval system module 116. In some embodiments, the querying operation 204 includes using a similarity metric to compare the maintenance cases in the knowledge database to the query in order to retrieve and rank the maintenance cases of the ranked list 138 of maintenance cases relating to the text query. For example, in one embodiment the querying operation 204 includes using Okapi BM25 similarity scores comparing the maintenance cases in the knowledge base to the query to retrieve and rank the ranked list of maintenance cases relating to the text query. The query operation 204 returns a ranked list of maintenance cases 138. As previously noted, each returned maintenance case of the ranked list 138 includes one or more part identifiers associated to the maintenance case (except for maintenance cases in which no parts were replaced).

At an operation 206, a topic modeling process 140 is performed on the maintenance cases of the ranked list 138 to group the maintenance cases into a number of N topics (where N is an integer greater than or equal to two). In some embodiments, the topic modeling process 140 groups maintenance cases of the ranked list 138 based on one or more selected properties of the cases, such as the product type of the maintenance case or the sub-system being serviced or the reported malfunction or some combination thereof. In other embodiments, the topic modeling process 140 includes using Latent Dirichlet Allocation (LDA) or another type of generative statistical model. In some embodiments, the topic modeling process 140 includes preprocessing, such as: performing tokenization and lemmatization of text of the maintenance cases of the ranked list 138 of maintenance cases; removing stop words or phrases contained in a predefined list of stop words and phrases (e.g., so as to remove common words that contain little domain-specific information, such as "the", "also", et cetera) from the maintenance cases of the ranked list; and performing the topic modeling 140 on the maintenance cases of the ranked list 138 cases after the preprocessing (e.g. illustrative tokenization, lemmatization, and removal of stop words).

At an operation 208, the replaced part identifiers 132 associated to the maintenance cases grouped into that topic are extracted and ranked (e.g., based on prevalence in the maintenance cases of that topic and/or ranking of the associated maintenance case in the ranked list 138) to generate a ranked replaced part identifiers list 142 for each topic. This operation can be performed by the topic modelling module 118. In some examples, the ranking operation 208 for the replaced part identifiers 132 for each topic is based on (i) frequency of occurrence of the replaced part identifiers in the maintenance cases grouped into that topic and (ii) the ranks of the maintenance cases grouped into that topic that contain the replaced part identifiers in the ranked list of maintenance cases.

At an operation 210, summarizations 144 of the N topics are displayed on the display device 105 of the service device 102, and a selection of a selected topic of the N topics is received via the service device 102 at the back end sever 111. The summarizations 144, for example, could include the ranked replaced parts identifiers lists 142 for the topics. In other examples, the summarizations 144 can include a list of report summaries of the highest ranked maintenance cases of each topic, if the maintenance cases include such summaries.

At an operation 212, a list 150 of recommended parts for replacements is displayed on the display device 105. The list 150 includes at least a top portion of the ranked replaced part identifiers list 142 for the selected topic of the display device 105. The top portion of the ranked replaced part identifiers list 142 can include a top "k" number of replaced part identifiers 132 on the ranked list 142. In some embodiments, the displaying operation 210 can include providing a parts ordering user interface (UI) 146 to the display device 105 of the service device 102 via which can the FSE can enter information to order replacement parts. The backend server 111 then receives a selection of one or more part identifiers 132 via the parts ordering user interface 146 and to connect via an electronic network 148 (e.g., the Internet) with the parts ordering system 100 to order one or more parts corresponding to the selected one or more part identifiers.

By contrast, the topic modeling 206 is omitted in a baseline process 220 (left-hand flow chart of FIG. 2). In the baseline process 220, the ranking operation 208 is applied directly to the maintenance cases of the ranked list 138 cases, and the list of recommended parts for replacement would then include all replacement parts associated to all maintenance cases of the ranked list 138. This is recognized herein to have substantial disadvantages compared with the process that includes the topic modeling 206. In the baseline process 220, the list of recommended parts for replacement produced by the baseline process commingles recommended parts for replacement amongst different types of maintenance tasks. Furthermore, the resulting list of recommended parts for replacement will be larger than the corresponding lists for the individual topics, since it will be a union of the lists for all N topics produced by the topic modeling 206. As a consequence, the list of recommended parts for replacement produced by the baseline process 220 will be difficult for the user to navigate and make use of By contrast, as recognized herein, the topic modeling 206 remedies these disadvantages by separating the maintenance cases of the ranked list 138 into groups (i.e. topics) with the cases of each group (topic) related to one another. The user can readily identify the topic most relevant to the current maintenance case, and thereby be presented with the list of recommended parts for replacement for only that topic.

EXAMPLE

In the foregoing, entity descriptions are composed of equipment characteristics and represented by maintenance cases registered in the system. Entities to be retrieved are parts recommended for replacement to troubleshoot a machine associated with a new maintenance case. Queries may contain various characteristics of new reports that should be treated by a maintenance service team. The entity, i.e. spare part is identified with a unique ID that is associated with a historical case description. One historical case can have several parts associated with it, similarly, a new service case may require a set of parts.

The knowledge base of maintenance cases is supported and updated with the help of service engineers, such as FSEs. They submit maintenance reports for every equipment issue or customer complaint as short technical texts often in multiple languages (i.e., English and a locally spoken language). The reports might contain abbreviations, software logs sent by a machine, short descriptions of a machine state on every step of the maintenance process. Closed cases are uploaded to the collection of historical cases that could be mined using the system 10.

To present the setting in a formal way, let q be a query, a case associated with the query is $c^{(q)}$, $P(c^{(q)})$ stands for parts replaced in the query case $c^{(q)}$. C(q) denotes all cases retrieved for the query q. A set of parts replaced in matched cases C(q) is denoted as PC (q)=$U_{c \in c(q)}$ P(c), and a set of ranked parts is expressed by r (q; C (q); PC (q))=PR.

The method 200 combines a baseline two-step entity retrieval setting and an add-on topic modelling component that groups search results under topics to improve retrieval performance.

The baseline entity search system is empowered with a two-step retrieval mechanism. A database of entity descriptions that contains target entities lies in the foundation of the mechanism. At the first step of the entity search, a system retrieves relevant descriptions using a Vector Space Model (VSM) with Okapi BM25 similarity score (see, e.g., Christopher D. Manning, Prabhakar Raghavan, and Hinrich Schutze. 2008. Introduction to Information Retrieval. Cambridge University Press, Cambridge. https://doi.org/10.1017/CBO9780511809071; S E Robertson, S Walker, K Sparck Jones, and M Hancock-Beaulieu. 1994. Okapi at TREC-3. Proceedings of the Third Text Retrieval Conference (1994)). This can be performed by the baseline entity retrieval system module 116. VSM is a document and query representation model that converts texts to N-dimensional vectors of term weights, where N is the number of words in a dictionary. Terms are simply words present in the document and query. The dictionary is built from a text corpus and includes words that appear in the documents. The intuition behind VSM is that retrieved documents will be ranked according to a similarity function computed for a query and a document, i.e. vectors in a vector space.

In this context, for a query q containing keywords $\{q_i\}_{j=1}^n$ and a maintenance case description c with fields $\{c_j\}_{i=1}^m$ Okapi BM25 similarity score could be expressed as follows:

$$BM25(q, c) = \sum_{i=1}^{n} \sum_{j=1}^{m} IDF(q_i) \cdot \frac{f(q_i, c_j) \cdot (k_1 + 1)}{f(q_i, c_j) + k_1 \cdot \left(1 - b + b \cdot \frac{L_{c_j}}{L_{avg j}}\right)} \quad (1)$$

Here, f ($q_i$, $c_j$) is the frequency of keyword $q_i$ in a field $c_j$ of case description c, $L_{c_j}$ is the length of the field $c_j$, i.e. number of words, and $L_{avg_j}$ is the average length of the field j in descriptions of all cases in a collection C. Variables k1 and b are tuning parameters that control how much every new occurrence of a term impacts the score and document length scaling correspondingly. Inverse Document Frequency is calculated as:

$$IDF(q_i) = \log\left(\frac{M - n(q_i) + 0.5}{n(q_i) + 0.5}\right), \quad (2)$$

where M is the total number of cases, i.e. M=|C|, and $n(q_i)$ is the number of case descriptions that contain the query term $q_i$. Therefore, the case $c^{i^1}$ is ranked higher than $c^{i^2}$ iff BM25 (q, $c^{i^1}$)>BM25(q, $c^{i^2}$).

The second step realizes the entity retrieval. This operation can be performed by the topic modelling module 118. It ranks spare parts associated with the retrieved cases based on the frequency of their occurrence and the rank of the case where they occur. Thus, the most frequent parts that occur in top ranked cases appear higher on the final list of retrieved parts than a part that appears the same number of times lower on the case list.

Transformation of the historical cases and parts retrieval pipeline is performed by adding a component that groups retrieved cases under a number of topics and ranks the parts within the topics. In the transformed pipeline, all retrieved cases are grouped by topics that they are assigned to by the topic modelling component. The parts used within each group are then ranked in a topic-based manner.

The topic modelling module 118 could be considered as an individual NLP pipeline with a number of steps. The pipeline includes tokenization and lemmatization steps, removal of stop phrases, building a dictionary of tokens, term weighting and topic modelling using Latent Dirichlet Allocation (LDA). Tokenization of the text refers to splitting it into units or tokens that represent individual words or sometimes groups of words. The process of lemmatization involves finding the initial forms, also referred to as root forms or lemmas, of the inflected words. A lemma is a word in its canonical form that exists in the dictionary of the used language. For example, the lemma for do, doing, did it the word do. Next, term weighting refers to assigning weights to tokens. The term frequency or bag-of-words weights is utilized as a term weighting scheme. It associates a weight proportional to the frequency of the term occurrence in the corpus of documents. LDA is a state-of-the-art algorithm for topic modelling that is based on generative probabilistic language model (see, e.g., David M. Blei, Andrew Y. Ng, and Michael T. Jordan. 2003. Latent Dirichlet Allocation. *Journal of Machine Learning Research* 3 (2003), 993-1022). The purpose of LDA is to learn the representation of a fixed number of topics and derive the topic distribution for every document in a collection. Every maintenance service case is assigned a topic according to the maximum probability of the case belonging to a topic.

Figure 4:
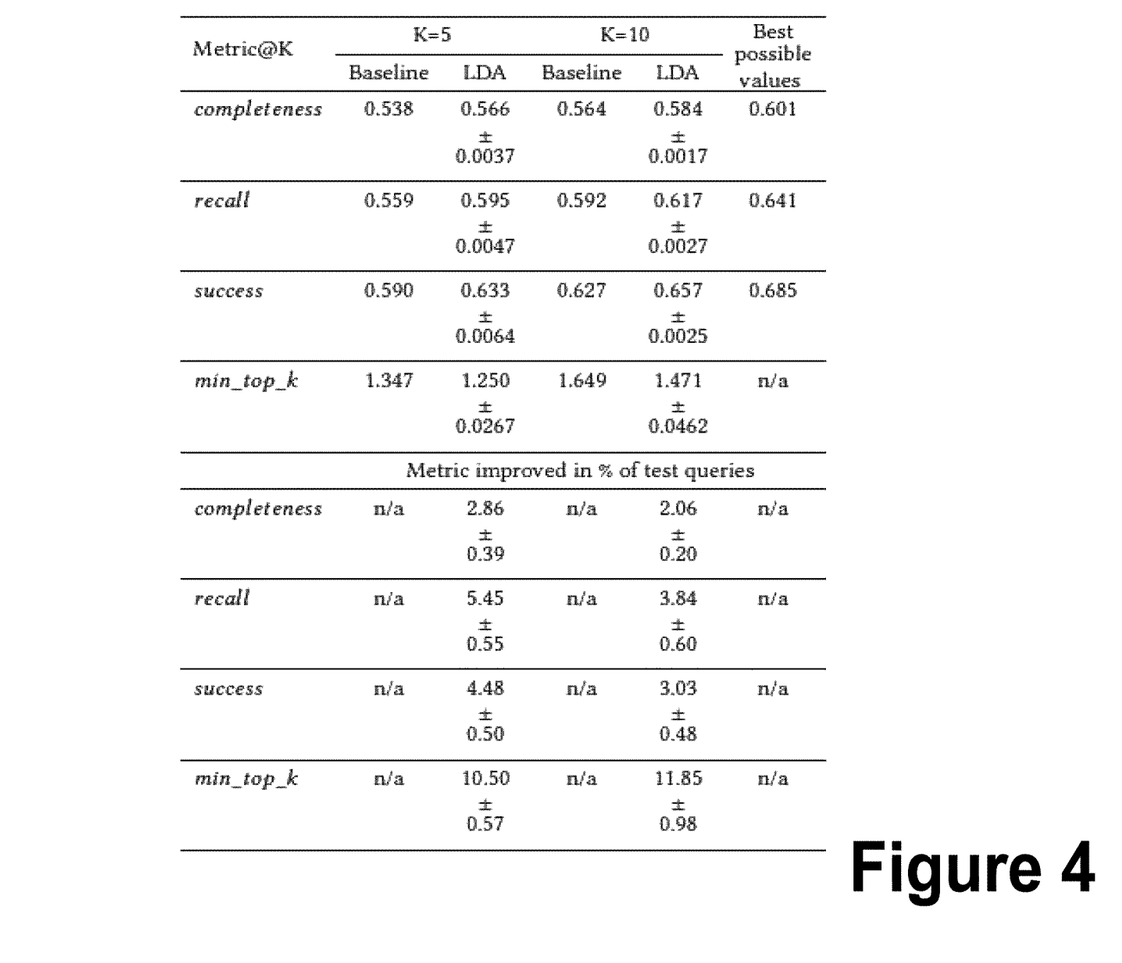

The experimental dataset is composed of historical maintenance cases. Each historical case has a number of associated logs such as time of customer complaint registration, a textual description of maintenance activities and parts used to solve the issue. Textual fields of every case have been combined into one description per maintenance case and serve as input to LDA training and testing stages. Case descriptions are usually stored in multiple languages: they contain descriptions in English and in the language spoken in the country of the case origin, i.e. where the supported equipment is installed. In detail, only 36.5% of cases in the initial dataset originate from the countries where English has been used as a main reporting language. FIG. 4 presents the distribution of the number of queries over their characteristics: the number of retrieved and ranked parts, maintenance service cases and parts replaced in the maintenance case associated with the performed query. The majority of queries retrieved 200 or less similar case descriptions, however, this number could reach up to 1000 cases. The number of unique recommended parts retrieved from these cases were 100 or less, while the number of parts required to treat a maintenance case associated with the query was 5 or less in the majority of cases.

A training set is composed of historical cases reported in English for which no query has been made and contains 101026 case descriptions. On the contrary, the test set consists of the cases for which a service engineer made a query to the historical cases database and retrieved similar cases. Therefore, a test set consists of 1564 pairs: (the case c(q) associated with a query q; a set of cases C(q) relevant for a query q). Cases returned for the queries may have non-empty intersection with the training dataset, however, the cases for which the queries had been created were excluded from the training set. Once a new case is closed it is added to the collection of historical cases and can be retrieved by future queries.

Top K ranked parts are used to estimate success, completeness,ecall and min_top_k metrics. They are defined in the following terms: let q be a query, a case associated with the query is $c^{(q)}$, $P(c^{(q)})$ stands for parts replaced in the query case $c^{(q)}$. C(q) denotes all cases retrieved for the query q. A set of parts replaced in matched cases (q) is denoted as $PC(q)=U_{c \in C(q)}P(c)$, and a set of ranked parts is expressed by r(q:C(q); PC(q))=PR. Metric@K is computed for a set of retrieved parts |PR|≤K. The operator |·| applied to a set defines it cardinality. The metrics are calculated as follows:

$$\text{completeness@}K(q) = \begin{cases} 1, & \text{if } P(c^{(q)}) \subseteq PR, \\ 0, & \text{if } P(c^{(q)}) \not\subseteq PR; \end{cases} \quad (3)$$

$$\text{success@}K(q) = \begin{cases} 1, & \text{if } |P(c^{(q)}) \cap PR| > 0, \\ 0, & \text{if } |P(c^{(q)}) \cap PR| = 0; \end{cases} \quad (4)$$

$$\text{recall@}K(q) = \frac{|P(c^{(q)}) \cap PR|}{|P(c^{(q)})|}; \quad (5)$$

$$\min\_\text{top}\_k@K(q) = k, k \leq K \text{ \& completeness@}k(q) = 1; \quad (6)$$

As a baseline initial part retrieval strategy and its statistics for the whole set of retrieved cases PC(q)=PR are used. Once topics are computed, the metrics are estimated for parts associated with the cases in every topic t, i.e. a subset of cases and, therefore, parts: $PR^{(t)}$={PC(q)|c∈ C(q)&c∈ t}. Completeness measures whether all the used parts were suggested for a new troubleshooting report, success shows if any consumed part was listed among retrieved parts and recall indicates the ratio of retrieved parts that were consumed to the total number of consumed parts. Query cases that were resolved without parts consumption, i.e. the cases $c^{(q)}$:|P($c^{(q)}$)|=0 are discarded. An additional metric min_top_k is used to estimate how far in the list of retrieved parts one can find the full list of consumed parts in the query case and returns null if such k does not exist.

The initial IR system is powered by Elasticsearc. It performs indexing of the documents in the knowledge base and retrieves them according to Okapi BM25 ranking with default tuning parameters $k_1=1.2$ and $b=0.75$.

For the add-on topic modelling component, Python NLP libraries are used; Gensim for all the steps including topic modelling and spaCy for lemmatization. One step that is also customized to the topic modelling application is removal of stop phrases. A collection of English stopwords pre-defined by Gensim and corpus-specific common phrases such as questionnaire forms repeated across the majority of cases are used, since question formulations do not characterize individual cases. Gensim library allows to vectorize documents using Tf and pass them as input to the LDA realization. The following NLP pipeline is used: Tf term weighing and documents vectorization followed by LDA topic modelling (LDA).

One characteristic of LDA model is that it provides different topic distribution depending on a random seed used in its initialization. Therefore, every LDA model with the same parameters should be computed several times that will be referred to as "runs". Afterwards, all the metrics should be averaged over several runs to get consistent results and minimize the influence of the algorithm's stochastic behavior. Another control parameter is the number of topics which spans from 5 to 20. All the metrics are evaluated at top K retrieved parts, K=5, 10. The algorithm is set up to learn symmetric $\alpha$, a document-topic prior, from data as well as $\eta$, a topic-word prior; the number of iterations is fixed at 100.

In addition, an empirical parameter for the ratio of English words appearing in the case description is set to REn=30%. A topic will be derived by LDA trained on the English corpus in case the description contains at least REn English words, otherwise the maintenance case will be marked as "topic undefined".

The performance of maintenance cases and parts retrieval in the initial configuration of part retrieval system (Baseline) with LDA topic modelling component is evaluated using the above described metrics at different K and compared to the best possible results on the test dataset computed at K=∞. The results are reported in Table 1. Comparing baseline results at different top K retrieved parts, it can be seen that the values of completeness, recall and success. increase with higher K and achieve the possible maximum K=∞. The values min_top_k@K increase as K grows, therefore, min_top_k@∞ is not a target value for this metric, since it is higher than the values of min_top_k@K for any K while the goal is to minimize it. Since the lowest min_top_k@K possible is desired, this metric is improved when the average value decreases.

Overall improvement is observed for the experimental configuration with two topic modelling pipelines. For metrics evaluated at K=10, the improvement reached 54%, 53% and 52% of maximum possible improvement for completeness, recall and success. It indicates that the introduced component effectively captures similar cases and therefore parts, too. The performance improvement influenced by topic modelling is more prominent at smaller values of K as can be seen from the difference between average baseline values of completeness, recall and success and those of LDA.

There is a stable increase in the ratio of improved queries for completeness, recall and success calculated at smaller K. For example, from less than 4% of queries for recall@10 to around 5.45% for recall@5. Turning now to the ratio of queries with improved min_top_k@K, it is higher for larger K since the set of top ranked parts increases with greater K likewise the probability of finding all the necessary parts among top K parts. Yet, min_top_k is the metric with the most prominent progress according to the ratio of queries that were improved using topic modelling: 10.50% to 11.85% for LDA configuration.

While for some queries the metrics are improved by the introduction of LDA component, 0.007% to 0.5% of queries experienced deterioration of the completeness, recall and success at different K metrics' values and 0.8% to 3.2% of queries for min_top_k@K. This happens, for example, when a number of documents with the right parts suggestion do not appear in the same group. A possible solution (as well as a future work direction) is to integrate domain knowledge into the system and pre-define the number of topics and their characteristic terms to always appear in the same topic.

Figure 5:
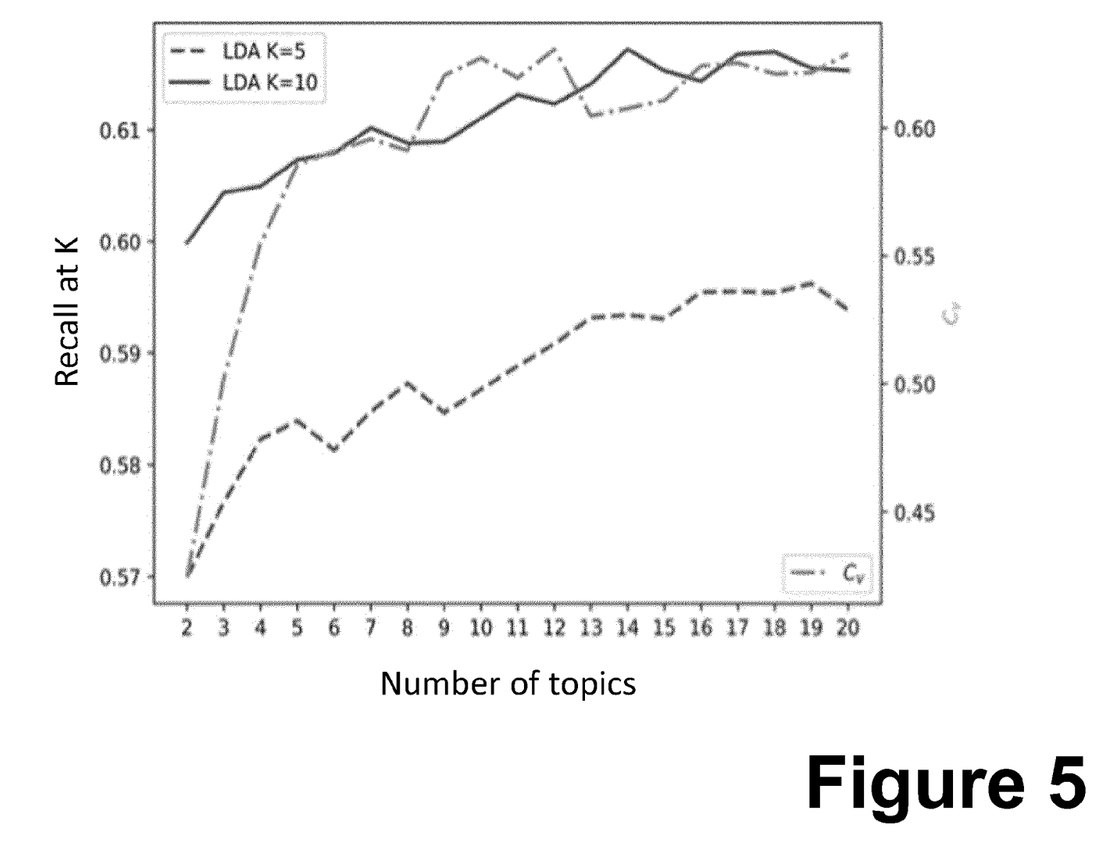

The queries are grouped by number of parts used in the query case and retrieved cases as well as by the number of retrieved service cases as demonstrated in FIG. 5. The queries made for service cases that did not require any part replacement are distinguished, and mark them as $|P(c^{(q)})|=0$. The groups of queries that benefited the most from the topic modelling component integration are the following: 1. queries with number of retrieved cases $|C(q)|>100$; 2. queries associated with cases that required $1 \leq |P(c(q))| \leq 10$ parts; 3. queries with retrieved and ranked parts $10<|PR| \leq 100$. Therefore, the topic modelling has a positive effect on the queries that result in extensive lists of cases and, thus, parts appearing in those cases.

LDA requires a number of topics to be passed as an input parameter. In some applications this number is available as expert knowledge or is motivated by the dataset. Alternatively, a set of coherence metrics could be used to indicate the semantic correspondences within and throughout the derived topics and to evaluate their quality. When a target number of topics is unknown, it could be suggested by the elbow method applied to coherence measures. The coherence score Cv measured over 5 LDA instantiations with 2-20 topics resulted in an elbow point at between 5 and 9 topics for LDA as shown in FIG. 5. However, the best results of IR evaluation metrics were obtained in the majority of experiments with LDA at K=5 for 18, 19 topics and at K=10 for 14 topics. In general, the models perform well with 13 or more topics. The impact of the number of topics in terms of chosen evaluation metrics is observed on a smaller scale for 13 or more topics than for the number of topics from 5 to 12.

Entity retrieval (ER) is defined in as the task of answering queries with a ranked list of entities. The area of entity retrieval is closely connected to IR and database search, NLP, and Semantic Web. Both IR and ER are usually enabled with a search engine, a user interface for passing a query and an available knowledge base. However, while IR aims at document retrieval, the target of ER is to provide a list of ranked relevant entities such as people, places, products or other specific concepts and things. An entity is characterized with a unique ID, a name and, depending on a system realization, a type, and a set of attributes. Data associated with the entity could be considered as its description in natural text or in a more structured form. NLP techniques are used for representation of unstructured texts in a knowledge base, query processing and expansion, named entity recognition and query-document modelling. It also facilitates context capturing, named entity recognition, topic-oriented filtering in IR and ER. Semantic Web has recently advanced in knowledge representation utilizing such tools and frameworks as ontologies, expert systems, knowledge graphs and linked data. Considering the stratification, the method 200 could be categorized as ad-hoc entity retrieval that uses semantically enriched term representation and preserves topical relations among search results.

Industries have been adopting process planning and knowledge-based systems for machine manufacturing and maintenance over the recent years. Following the categorization of AI-based data approaches for system health management into knowledge and data-driven classes that include expert systems and machine learning algorithms respectively, the method 200 applies to the area of hybrid models that tend to combine data and knowledge-driven approaches.

The work on technical support utilizing a historical case base can be particularly relevant. The goal of the method 200 is to aid telecom technical support teams with a fast and accurate search over the solutions base for previously registered cases and solutions from other technical texts. A method of populating an existing ontology has been proposed using text segmentation and scoring to serve the use case of Telecom Hardware remote user assistance.

Effectiveness of IR systems could be improved by topic modelling that mines term associations in a collection of documents. Topic modelling could be integrated to IR tasks to smooth the document model with a document term prior estimated using term distributions over topics. The work explores the ways of modelling term associations as a way of related terms integration into document models and proposes a model of probabilistic term association using joint probability of terms.

The following relates to a way of improving a spare part retrieval system for remote diagnostics and maintenance of medical equipment by applying topic modelling to search results. The topic modelling component was used to cluster the results of a baseline retrieval system and improve the relevance of the search results. Decision-making process of maintenance service teams that search in a historical collection of troubleshooting reports and retrieve parts needed for a new similar issue are supported. The experimental dataset was constructed from query-result pairs pointing at the historical case base and parts used in the cases. Several IR metrics are adjusted to evaluate the results of spare part retrieval in the baseline architecture and using the topic modelling component. The major enhancement is observed for the metric that estimates the minimum top ranked parts that are sufficient for the full treatment of a service case associated with a performed query. A natural progression of this work is to apply online topic learning and automatically recommend the topic that performs best for a given query. An input from domain experts would help fix the number of topics and characteristic terms that should appear under one topic. Furthermore, additional domain knowledge could be combined with the entity retrieval system under consideration to suggest actions beyond part replacement, such as troubleshooting tests for remote and on-site diagnostics.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A medical parts ordering system operative in conjunction with a knowledge base of maintenance cases for medical devices under maintenance wherein the maintenance cases have associated replaced part identifiers, the medical parts ordering system comprising:
   a user interface device including a display and at least one user input device;
   a knowledge base of maintenance cases for medical devices, wherein the knowledge base includes information about the medical device of the corresponding maintenance case, wherein the information includes information securely transferred from the medical device to knowledge base and is correlated to the solution of the maintenance case; and
   an electronic processor programmed to perform a recommendation method for recommending parts for replacement during maintenance of a device currently under maintenance, the recommendation method including:
      receiving a text query relating to the maintenance of the device currently under maintenance via the user interface device;
      querying the knowledge base of maintenance cases using the text query to compare against the maintenance case and information received from the corresponding medical device of the maintenance case to retrieve a ranked list of maintenance cases relating to the text query;
      performing topic modeling on the maintenance cases of the ranked list of maintenance cases to group the maintenance cases into N topics, where N is an integer greater than or equal to two;
      for each topic, ranking the replaced part identifiers associated to the maintenance cases grouped into that topic to generate a ranked replaced part identifiers list for that topic;
      displaying summarizations of the N topics on the display of the user interface and receiving a selection of a selected topic of the N topics via the user interface device; and
      displaying a list of recommended parts for replacement comprising at least a top portion of the ranked replaced part identifiers list for the selected topic on the display of the user interface device, wherein the displaying of the list of recommended parts for replacement is included in a parts ordering user interface presented on the user interface device, and the electronic processor is further programmed to:
         receive a selection of one or more part identifiers via the parts ordering user interface and to connect via an electronic network with a parts ordering system to order one or more parts corresponding to the selected one or more part identifiers.

2. The medical parts ordering system of claim 1, wherein the performing of topic modeling comprises performing topic modeling using Latent Dirichlet Allocation (LDA).

3. The medical parts ordering system of claim 1, wherein the performing of topic modeling comprises:
   performing tokenization and lemmatization of text of the maintenance cases of the ranked list of maintenance cases;

removing stop words or phrases contained in a list of stop words and phrases from the maintenance cases of the ranked list of maintenance cases; and performing the topic modeling on the maintenance cases of the ranked list of maintenance cases after the tokenization, lemmatization, and removal of stop words.

4. The medical parts ordering system of claim 1, wherein the ranking of the replaced part identifiers for each topic is based on (i) frequency of occurrence of the replaced part identifiers in the maintenance cases grouped into that topic and (ii) the ranks of the maintenance cases grouped into that topic that contain the replaced part identifiers in the ranked list of maintenance cases.

5. The medical parts ordering system of claim 1, wherein the querying of the knowledge base using the text query to retrieve the ranked list of maintenance cases relating to the text query includes:

using a similarity metric to compare the maintenance cases in the knowledge database to the query in order to retrieve and rank the maintenance cases of the ranked list of maintenance cases relating to the text query.

6. The medical parts ordering system of claim 1, wherein the querying of the knowledge base using the text query to retrieve the ranked list of maintenance cases relating to the text query includes:

using Okapi BM25 similarity scores comparing the maintenance cases in the knowledge base to the query to retrieve and rank the ranked list of maintenance cases relating to the text query.

* * * * *